(12) United States Patent
Channer

(10) Patent No.: US 7,036,747 B2
(45) Date of Patent: May 2, 2006

(54) AIR FRESHENING DEVICES

(75) Inventor: Robert Vern Channer, Oxon (GB)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 10/473,111

(22) PCT Filed: Mar. 27, 2002

(86) PCT No.: PCT/GB02/01419

§ 371 (c)(1),
(2), (4) Date: Sep. 29, 2003

(87) PCT Pub. No.: WO02/078750

PCT Pub. Date: Oct. 10, 2002

(65) Prior Publication Data

US 2004/0094636 A1   May 20, 2004

(30) Foreign Application Priority Data

Mar. 29, 2001 (GB) .................................... 0107861

(51) Int. Cl.
*A24F 25/00* (2006.01)

(52) U.S. Cl. .......................... 239/60; 239/57; 422/123; 424/76.4

(58) Field of Classification Search ................. 239/34, 239/57, 58, 60; 422/123, 124; 424/76.3, 424/76.4
See application file for complete search history.

(56) References Cited

U.S. PATENT DOCUMENTS

| 4,502,630 A | 3/1985 | Haworth et al. |
| 4,572,375 A | 2/1986 | Baer |
| 5,230,867 A | 7/1993 | Kunze et al. |
| 5,419,879 A | 5/1995 | Vlahakis et al. |
| 5,439,100 A | 8/1995 | Gordon et al. |
| 6,080,367 A | 6/2000 | Lin |
| 6,631,852 B1 * | 10/2003 | O'Leary ...................... 239/60 |

FOREIGN PATENT DOCUMENTS

| EP | 0321729 A2 | 6/1989 |
| EP | 1076014 A2 | 2/2001 |
| WO | WO 98/00179 A1 | 1/1998 |
| WO | WO 00/24434 | 5/2000 |

OTHER PUBLICATIONS

PCT International Search Report for GB02/01419 dated Jul. 5, 2002.

(Continued)

*Primary Examiner*—Steven J. Ganey
(74) *Attorney, Agent, or Firm*—Norris McLaughlin & Marcus PA

(57) ABSTRACT

The invention relates to improvements in or relating to containers and in particular to a refill for an air freshening or purifying device utilizing a gel fragrance or other gel composition and to a device comprising a base container and a refill. The invention specifically comprises a refill for use with an air freshening or purifying device, said refill comprising a refill container having a gel receiving surface and an opposing rear surface, the gel receiving surface having at least one recess in which is contained a gel composition, wherein the profile of the rear surface inversely corresponds to the profile of the gel receiving surface such that it is provided with at least one projection inversely corresponding to the said recess in the gel receiving surface.

16 Claims, 1 Drawing Sheet

OTHER PUBLICATIONS

Combined Search and Examination Report dated Aug. 21, 2001 from The Patent Office in Great Britain for application GB 0107861.7.

Combined Search and Examination Report dated Aug. 23, 2002 from The Patent Office in Great Britain for application GB 0207151.2.

* cited by examiner

AIR FRESHENING DEVICES

The invention relates to improvements in or relating to containers and in particular to an air freshening or purifying device utilising a gel fragrance or other gel composition comprising a base container and refill kit.

U.S. Pat. No. 5,780,527 describes a gel which can be used as a fragrancing component in an air freshening device. This gel is particularly advantageous in that it can be used in attractively shaped open containers without the need for sealing. One air freshening device which is currently on the market comprises an attractive glass open sided container, which is recessed to form a dish with a base and circumferential side wall. The dish stands upright on a flattened section of its perimeter. A plurality of ridges are provided on the inner surface of the container base defining channels between the ridges, in which the gel is retained. As the fragrance is dissipated over time, the gel shrinks and cracks and is no longer wholly supported by the ridge walls. To prevent the shrinking gel from falling out of the container, a number of smallish channels are used, which are fairly narrow or have narrow sections.

It is desirous for the consumer to have a means of refilling the container once the gel fragrance has dissipated. However, as the filling process comprises the steps of filling the channels with the gel in liquid form and allowing the gel to set, this is not a process which the consumer is able to carry out.

It is therefore an object of the present invention to provide an air freshening or purifying device which utilises a gel fragrance or other gel composition supplied in a refill container.

According to the present invention there is therefore provided an air freshening or purifying device comprising a primary container having a gel receiving surface having at least one recess for receiving a gel composition, and a refill container having a gel receiving surface profiled to correspond to the gel receiving surface of the primary container and having at least one recess for receiving a gel composition, said refill container further having an opposing rear surface the profile of which inversely corresponds to the gel receiving surface of the primary container and is dimensioned so as to abut closely with and interlock with the gel receiving surface of the primary container so as to be retained thereby.

The refill container is preferably made from plastic material. The thickness of the refill container is preferably substantially uniform.

The refill container is preferably transparent or translucent. It is desirably clear although it may be coloured, for example, to match the colour of the gel or to provide a visual indicator of the scent of the gel or to match the colour of the container.

Preferably the gel receiving surfaces comprise a plurality of channels and ridges. Desirably the device has from 2 to 6 channels.

The gel composition is preferably a fragrance or air purifying composition, or an insecticide. The gel may be as described in, for example, U.S. Pat. No. 5,780,527. Thus it is, for example, a gel resulting from the cross-linking, in situ, of a homopolymer or copolymer in the presence of a perfuming, deodorising or insecticidal base. A suitable copolymer is maleinised polybutadiene or polyisoprene such as Lithene N4-9000 10MA (Registered Trade Mark) obtainable from Revertex Ltd. A suitable cross-linking agent, for example, a diamine, being a low molecular weight "polymer" containing two amine groups per molecule sold under the name Jeffamine 400 (Registered Trade Mark) obtainable from Huntsman Corp.

The material from which the refill container is made may have a substantially similar refractive index to the air freshening or purifying device with which it is intended to be used. Ideally the difference between the refractive indices is +/− 0.15 units, although more preferably it is zero.

Preferably there is no air gap between the container and the refill container. Either a composition may be provided between the two containers to exclude any air gap or the containers are dimensioned so as to exclude any air gap. Preferably the composition should have a refractive index lying between those of the containers.

A preferred embodiment of the present invention will now be described, by way of example only, with reference to the accompanying drawings in which.

Figure 1:
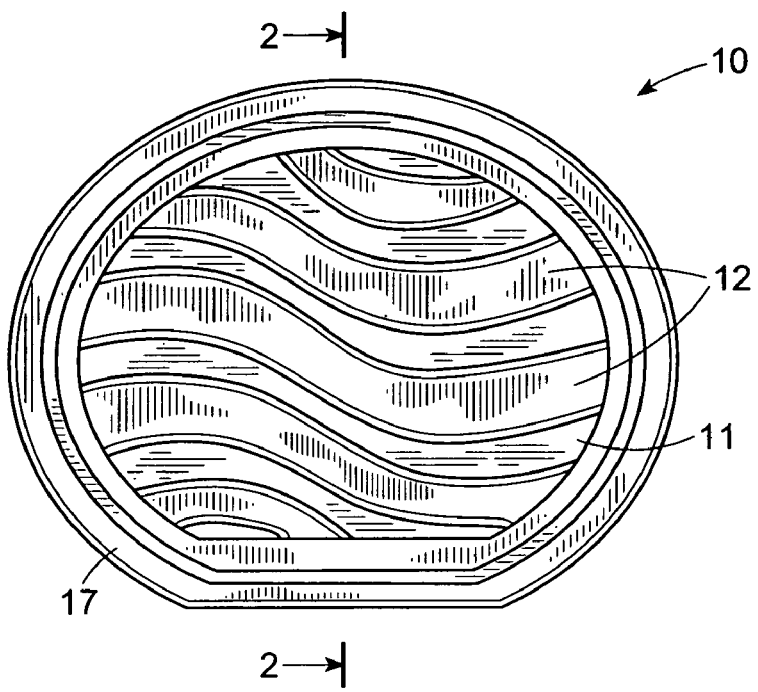
FIG. 1 is a front elevation of an air freshening device with which the refill container of the present invention is to be used.
Figure 2:
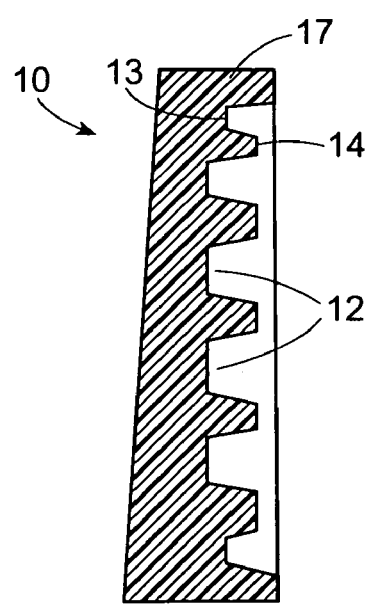
FIG. 2 is a cross-sectional side elevation of the air freshening device of FIG. 1 on the line II—II.
Figure 3:
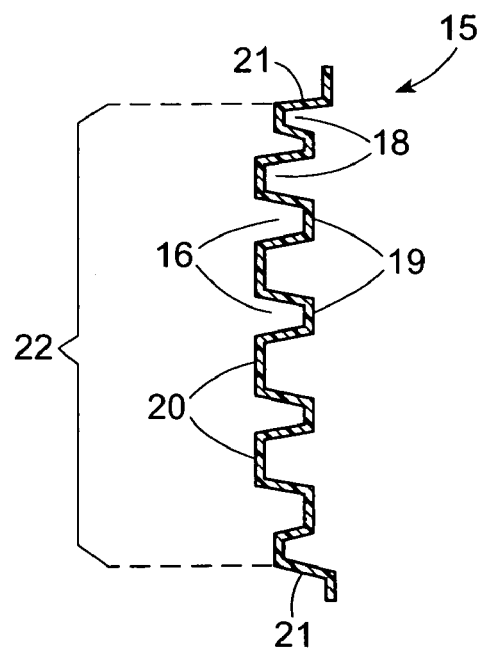
FIG. 3 is a cross-sectional side elevation of a refill container for use with the device of FIG. 1.

Referring to FIG. 1 there is shown an air freshening (or purifying) device 10. The device 10 comprises a container 11 having a base 13 and preferably a circumferential side wall 17. Although the container 11 illustrated is substantially circular, other shapes can easily be used. The container 11 is preferably made from clear, translucent and/or coloured glass, although other suitable reasonably rigid impermeable materials could be used.

On the inner surface of the container base 13 are provided a series of projections in the form of ridges 14, defining therebetween recesses in the form of channels 12. The profile of the ridges 14 is not limited to that shown. It is preferred that some or part of the channels 12 are reasonably narrow in this embodiment to hold the gel where it shrinks or cracks, or that additional means are provided to help hold the gel in the recesses. The channels 12 and ridges 14 may be formed by either recessing the base 13 or adding the ridges 14 to the base 13. The channels 12 and ridges 14 preferably provide an attractive pattern. The inner surface of the side wall 17, the inner surface of the base 13 and the profiled surface formed by the surfaces of the channels 12 and ridges 14 form a gel receiving surface. When the container 11 is filled with a gel composition, preferably of the type described in U.S. Pat. No. 5,780,527, which is preferably strongly coloured, the shape of the channels 12 is highlighted to give an attractive appearance.

An alternative air freshening device (not shown) may have a single recess for receiving the gel in an otherwise planar surface of the base 13.

In accordance with the invention, a refill container 15 is provided for use either when the original gel composition in the air freshening device 10 has dissipated or to avoid the need for initial filling of the device 10. The refill container 15 is preferably made of a transparent plastic or other impermeable material. Prime examples of suitable materials are APET, PETG, Polypropylene and Polyacrylonitrile as these have a high degree of clarity, are easy to thermoform and are resistant to attack by perfume. Further materials may comprise Polyethylene and Nylon, although these tend to be translucent or of a milky appearance, or PVC, Polystyrene and Styrene-Acrylonitrile, although these may be susceptible to fragrance attack.

The refill container 15 may also be translucent and/or coloured, for use with an air freshening device 10 which has a container 11 which is translucent and/or coloured. The colour used may be suggestive of the fragrance of the gel composition, e.g. yellow for lemon, pink for rose etc. The thickness of the material of the refill container 15 is preferably substantially uniform.

The refill container 15 also preferably has a circumferential sidewall 21, and a base 22 having at least one recess. In the embodiment illustrated the base is formed by a plurality of channels 18 defined by ridges 19, the upper profile of which preferably matches that of the original container 11, although this is not strictly necessary. The inner surfaces of the sidewall 21 and base 22 and the surfaces of the ridges 19 and channels 18 form a gel receiving surface. However the profile of the opposing rear surface of the container 15, preferably inversely corresponds to the profile of the gel receiving surface, such that it has at least one projection inversely corresponding to the at least one recess. In the embodiment illustrated, where the gel receiving surface has a plurality of ridges 19 the rear surface of the refill container 15 has a plurality of recesses 16 which are sized to receive the ridges 14 of the main container 11. Similarly where there are a plurality of channels 18 in the gel receiving surface of refill container 15, these form a plurality of ridges 20 in the rear surface of the container 15. These ridges 20 are sized to fit in the channels 12 of the container 11. The refill container 15 is filled with the gel composition in a similar manner to the container 11.

Once the gel composition in the original air freshening device 10 has dissipated, and any residue removed from the container 11, the refill container 15 can be positioned so that its rear surface abuts the gel receiving surface of the container 11.

Alternatively the air freshening device 10 may be sold with a refill container 15 already in situ. This advantageously eliminates the need for cleansing the container 15 before it can be used with a refill.

Where the materials used for both containers 11, 15 are transparent or are of the same colour, the refill container 15 cannot be seen as a separate component from the container 11. To enhance this it is preferred that the refractive indices of the materials of the containers 11, 15 are substantially the same and that the abutting profiles are sized and shaped so as to ensure there is no air gap between the containers 11, 15. However, the difference between the refractive indices of the material is preferably +/- 0.15 units and more preferably zero. Alternatively a composition may be provided between the containers 11, 15 to exclude any air gap therebetween. In this case the composition ideally has a refractive index lying between that of the containers 11, 15 or, if they have the same refractive index, the same as that.

The relative sizing and interlocking nature of the profiles of the containers 11, 15 ensures that the refill container 15 is held firmly in position by the container 11, although a releasable adhesive could be used to ensure this.

Once the gel composition in the refill container 15 has dissipated over time, the refill container 15 can simply be removed from the container and a new one inserted.

The refill container 15 is manufactured by a suitable method, such as vacuum forming, thermoforming or injection moulding. The channels 18 are then filled with the gel composition in liquid form and the gel allowed to set.

The refills can conveniently be provided with a removable lid, in the form of a tear off plastic or foil cover, to protect the gel before use. The shape of the refills also allows them to conveniently be stacked, so that a number can be sold together in a tube packaging.

The refill may be filled with a gel fragrance, which would provide as air freshening action, or with other gel based air purifying compositions, such as insecticides or disinfectants. Thus one container 11 could be used for a variety of different applications, merely by changing the refill container 15 filled with the required composition.

The invention claimed is:

1. An air freshening or purifying device (10) comprising a primary container (11) having a gel receiving surface (12, 14) having at least one recess (12) adapted for receiving a gel composition and at least one ridge (14) to hold the gel in the at least one recess (12), when the device is positioned with the gel receiving surface (12, 14) in a vertical orientation, and a refill container (15) having a gel receiving surface (18, 19) profiled to correspond to the gel receiving surface (12, 14) of the primary container (11) and having at least one recess (18) for receiving a gel composition and at least one ridge (19) to hold the gel in the at least one recess (18), said refill container (15) further having an opposing rear surface (16, 20) the profile of which inversely corresponds to the gel receiving surface (12, 14) of the primary container (11) and is dimensioned so as to abut closely with and interlock with the gel receiving surface (12, 14) of the primary container (11) so as to be retained thereby.

2. A device (10) as claimed in claim 1 in which the refill container (15) is made from a plastics material.

3. A device (10) as claimed in claim 1 in which the thickness of the refill container (15) is substantially uniform.

4. A device (10) according to claim 1 in which the refill container (15) is transparent.

5. A device (10) according to claim 1 in which the refill container (15) is translucent.

6. A device (10) according to claim 1 in which the refill container (15) is coloured.

7. A device (10) according to claim 1 in which the gel receiving surfaces comprise a plurality of recesses (12,18) and ridges (14,19).

8. A device (10) as claimed in claim 7 in which there are from 2 to 6 recesses (12,18) in the gel receiving surfaces.

9. A device (10) according to claim 1 in which the gel composition is a fragrance.

10. A device (10) according to claim 1 in which the gel composition is an insecticide.

11. A device (10) according to claim 1 in which the material from which the refill container (15) is made has a substantially identical refractive index to the primary container (11).

12. A device (10) according to claim 1 in which the difference between the refractive indices of the material from which the refill container (15) is made and that of the primary container (11) is +/−0.15 units.

13. A device (10) according to claim 1 in which there is no air gap between the primary container (11) and the refill container (15).

14. A device (10) as claimed in claim 13 in which a composition is provided between the two containers (11,15) to exclude any air gap.

15. A device (10) as claimed in claim 14 in which the refractive index of the composition lies between the refractive indices of the two containers (11,15).

16. A device (10) as claimed in claim 13 in which the containers (11,15) are dimensioned so as to exclude any air gap.

* * * * *